(12) United States Patent
Liebenberg et al.

(10) Patent No.: US 8,951,977 B2
(45) Date of Patent: Feb. 10, 2015

(54) AMORPHOUS ROXITHROMYCIN COMPOSITION

(75) Inventors: Wilna Liebenberg, Potchefstroom (SA); Marique Aucamp, Potchefstroom (SA)

(73) Assignee: North-West University (ZA)

( * ) Notice: Subject to any disclaimer, the term of this patent is extended or adjusted under 35 U.S.C. 154(b) by 70 days.

(21) Appl. No.: 13/640,643

(22) PCT Filed: Apr. 14, 2011

(86) PCT No.: PCT/IB2011/051621
§ 371 (c)(1),
(2), (4) Date: Dec. 21, 2012

(87) PCT Pub. No.: WO2011/128869
PCT Pub. Date: Oct. 20, 2011

(65) Prior Publication Data
US 2013/0102550 A1  Apr. 25, 2013

(51) Int. Cl.
*A61K 31/70* (2006.01)
*C07H 17/08* (2006.01)

(52) U.S. Cl.
CPC ..................................... *C07H 17/08* (2013.01)
USPC ............................... 514/29; 536/7.2; 536/7.4

(58) Field of Classification Search
USPC .................................................. 536/7.2, 7.4
See application file for complete search history.

(56) References Cited

PUBLICATIONS

"International Application Serial No. PCT/IB2011/051621, International Search Report mailed Aug. 12, 2011", 2 pgs.
"International Application Serial No. PCT/IB2011/051621, Written Opinion mailed Aug. 12, 2011", 8 pgs.
Biradar, S. V, et al., "A comparative study of approaches used to improve solubility of roxithromycin", *Powder Technology*, 169(1), (2006), 22-32.
Du Plessis, C., "Characterisation of polymorphic, pseudopolymorphic and amorphous forms of roxithromycin", *Thesis, North-West University: Potchefstroom Campus*, (2004), 194 pgs.
Mallet, F., et al., "Solvent Exchanges Among Molecular Compounds—Two extreme cases of pharmaceutical interest", *Journal of Thermal Analysis and Colormetry*, 72(2), (2003), 459-471.

*Primary Examiner* — Elli Peselev
(74) *Attorney, Agent, or Firm* — Schwegman Lundberg & Woessner, P.A.

(57) ABSTRACT

This invention relates to a macrolide composition, more particularly an amorphous form (Form-III) of 3R, 4S, 5S, 6R, 7R, 9R, 11S, 12R, 13S, 14R-6-[(2S,3R,4S,6R)-4-dimethylamino-3-hydroxy-6-methyloxan-2-yl]oxy-14-ethyl-7,12,13-trihydroxy-4-[(2R,4R,5S,6S)-5-hydroxy-4-methoxy-4,6-dimethyloxan-2-yl]oxy-10-(2-methoxyethoxymethoxyimino)-3,5,7,9,11,13-hexamethyl-1-oxacyclotetradecan-2-one or roxithromycin characterized by the absence of peaks in the infra-red spectrum of amorphous (Form-I11) of roxithromycin at 3577.15; 3526.03; 3465.27 and 3276.24 cm-1 relative to the infra-red spectrum of the prior art roxithromycin raw material displaying peaks at 3577.15; 3526.03; 3465.27 and 3276.24 cm-1 and further characterized by an increased solubility of at least 50% over prior art anhydrous and monohydrated roxithromycin in acetate buffer (pH 4.5), phosphate buffer (pH 6.8) and water.

12 Claims, 8 Drawing Sheets

AMORPHOUS ROXITHROMYCIN COMPOSITION

RELATED APPLICATION

This application is a nationalization under 35 U.S.C. 371 of PCT/IB2011/051621, filed Apr. 14, 2011 and published as WO 2011/128869 A1 on Oct. 20, 2011, which claimed priority to South African Patent Application Serial No. 2010/02670, filed Apr. 16, 2010; which applications and publication are incorporated herein by reference and made a part hereof.

INTRODUCTION AND BACKGROUND TO THE INVENTION

This invention relates to a macrolide composition. More particularly, this invention relates to a method of increasing the solubility of 3R, 4S, 5S, 6R, 7R, 9R, 11S, 12R, 13S, 14R-6-[(2S,3R,4S,6R)-4-dimethylamino-3-hydroxy-6-methyloxan-2-yl]oxy-14-ethyl-7,12,13-trihydroxy-4-[(2R,4R,5S,6S)-5-hydroxy-4-methoxy-4,6-dimethyloxan-2-yl]oxy-10-(2-methoxyethoxymethoxyimino)-3,5,7,9,11,13-hexamethyl-1-oxacyclotetradecan-2-one or roxithromycin. This invention further relates to a novel polymorph, (Form-III), of roxithromycin.

Roxithromycin, a 14-membered-ring, macrolide antibiotic, is very similar in composition, chemical structure (semi-synthetic) and mechanism of action to erythromycin. Roxithromycin is currently available in two forms, namely anhydrous and monohydrate form.

Roxithromycin exhibits activity against some sexually transmitted diseases, upper and lower respiratory tract infections, asthma, gum infections like gingivitis, and bacterial infections associated with stomach and intestinal ulcers. Roxithromycin is further regarded as the drug of choice for the treatment of opportunistic infections occurring in HIV/AIDS patients owing to its activity against *Cryptosporidium* spp., *Mycobacterium avium* complex, *Pneumocystis carinii* and *Toxoplasma gondii*.

A disadvantage associated with roxithromycin is that it is a hydrophobic molecule because it has no free hydroxyl group and is thus poorly water-soluble and unstable in an acidic environment.

A further disadvantage associated with roxithromycin is that its poor water-solubility and instability in an acidic environment result in a decrease in the absorption and bioavailability thereof.

Yet another disadvantage of roxithromycin is that said decreased absorption and bioavailability require relatively large quantities of roxithromycin to be administered in order to achieve a therapeutic effect.

A disadvantage associated with the use of relative large quantities of roxithromycin is that there is a potential increase in the side-effects associated with this active ingredient.

An even further disadvantage associated with the use of relative large quantities of roxithromycin is that there is an increase in the production and manufacturing cost of roxithromycin dosage forms, thereby increasing the cost of treatment.

OBJECT OF THE INVENTION

It is accordingly an object of the present invention to provide a novel polymorph, Form-III, of roxithromycin. Another object of the invention is to provide a preparation method for increasing the solubility of roxithromycin. Yet another object of the invention is to provide a medicament prepared in accordance with such a method with which the aforesaid disadvantages may be overcome or at least minimised.

SUMMARY OF THE INVENTION

According to the first aspect of the invention there is provided a composition comprising an amorphous form (Form-III) of roxithromycin.

The amorphous form (Form-III) of roxithromycin may have an infra-red spectrum displaying no peaks at 3577.15; 3526.03; 3465.27 and 3276.24 cm$^{-1}$ relative to the roxithromycin raw material, which displays peaks at 3577.15; 3526.03; 3465.27 and 3276.24 cm$^{-1}$.

Figure 4:
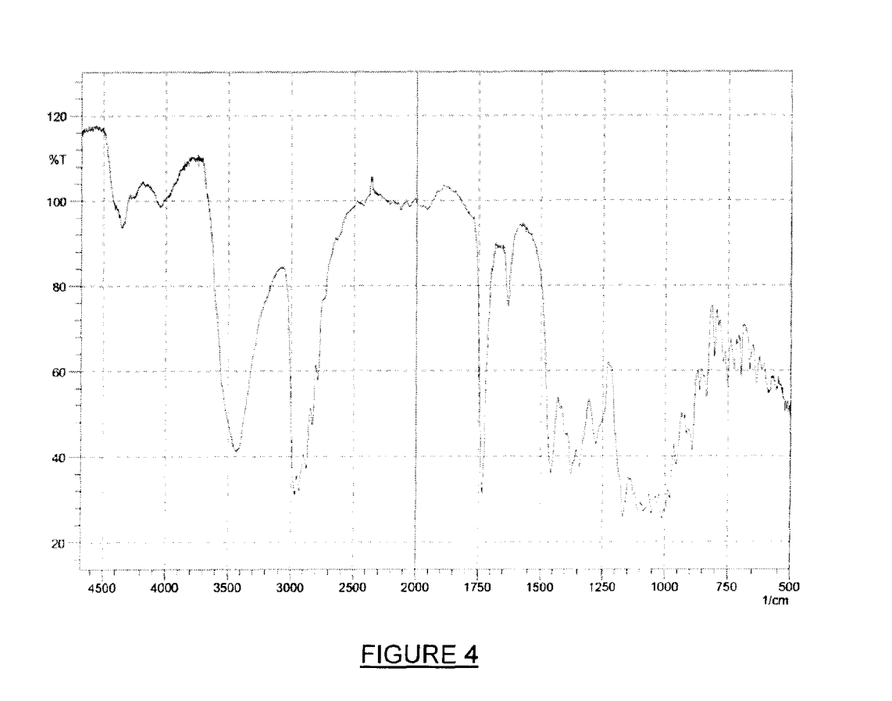

The amorphous form (Form-III) of roxithromycin may display an infra-red spectrum substantially as depicted in FIG. 4.

The amorphous form (Form-III) of roxithromycin may have at least 50%, preferably at least 150%, increased solubility over anhydrous and monohydrated roxithromycin in acetate buffer (pH 4.5).

The amorphous form (Form-III) of roxithromycin may have at least 50%, preferably at least 100%, increased solubility over anhydrous and monohydrated roxithromycin in phosphate buffer (pH 6.8).

The amorphous form (Form-III) of roxithromycin may have at least 50%, preferably at least 150%, increased solubility over anhydrous and monohydrated roxithromycin in water.

According to a second aspect of the invention there is provided a method of increasing the solubility of roxithromycin including the steps of providing roxithromycin selected from the group consisting of anhydrous roxithromycin and monohydrated roxithromycin; dissolving the roxithromycin in an organic solvent; allowing the organic solvent to evaporate to render the roxithromycin in a crystalline form; and allowing the crystalline roxithromycin to desolvate, to render the roxithromycin in an amorphous form (Form-III) of roxithromycin.

The organic solvent may be selected from a group consisting of 1,4-dioxane, 1-butanol, 1-propanol, 2-butanol, 2-propanol, acetic acid, acetone, acetonitrile, benzene, chloroform, dichloromethane, diethyl ether, dimethylformamide, ethanol, ethyl acetate, heptanol, hexane, hexanol, mesitylene, methanol, octanol, pentanol, petroleum ether, propionic acid, tetrahydrofuran and toluene. The organic solvent is preferably chloroform.

The step of dissolving the roxithromycin in the organic solvent includes the further step of preparing a supersaturated solution of the roxithromycin in the organic solvent.

According to a third aspect of the invention there is provided amorphous form (Form-III) of roxithromycin prepared from anhydrous or monohydrated roxithromycin in accordance with the method of the second aspect of the invention.

According to a fourth aspect of the invention there is provided use of a medicament prepared according to the second aspect of the invention together with at least one inert pharmaceutically acceptable carrier or diluents in a dosage form selected from the group consisting of tablets; capsules; powders; solutions; syrups; suspensions; bolus injections; continuous infusions; powder for reconstitution; ointments; creams; gels; lotions; sprays enemas, douche, pessaries, transdermal patches, dermal patches and lozenges.

According to a fifth aspect of the invention there is provided a method of treating a patient suffering from any one or more of the conditions selected from a group consisting of sexually transmitted diseases, upper and lower respiratory tract infections, asthma, gum infections, bacterial infections associated with stomach and intestinal ulcers and opportunistic infections associated with immune deficiency conditions including the step of administering to such a patient a pharmaceutically effective amount of amorphous polymorphic form, (Form-III) of roxithromycin prepared in accordance with the method of the second aspect of the invention.

According to a sixth aspect of the invention there is provided use of a pharmaceutically effective amount of an amorphous form, (Form-III) of roxithromycin prepared in accordance with the method of the second aspect of the invention in a method of treating a patient suffering from any one or more of the conditions selected from a group consisting of sexually transmitted diseases, upper and lower respiratory tract infections, asthma, gum infections, bacterial infections associated with stomach and intestinal ulcers and opportunistic infections associated with immune deficiency conditions.

According to a seventh aspect of the invention there is provided use of a pharmaceutically effective amount of an amorphous form, (Form-III) of roxithromycin prepared in accordance with the method of the second aspect of the invention in a method of preparing a medicament for use in treating a patient suffering from any one or more of the conditions selected from a group consisting of sexually transmitted diseases, upper and lower respiratory tract infections, asthma, gum infections, bacterial infections associated with stomach and intestinal ulcers and opportunistic infections associated with immune deficiency conditions

BRIEF DESCRIPTION OF THE FIGURES

The invention will now be described further, by way of non-limiting examples only, with reference to the accompanying figures wherein.

DESCRIPTION OF A PREFERRED EMBODIMENT OF THE INVENTION

According to a preferred embodiment of the invention there is provided a method for increasing the solubility of roxithromycin and for preparing a novel amorphous polymorph form, (Form-III) of roxithromycin.

The method includes the steps of selecting roxithromycin from the group consisting of anhydrous roxithromycin and monohydrated roxithromycin; dissolving the roxithromycin in an organic solvent; allowing the organic solvent to evaporate to render the roxithromycin in a crystalline form; and subsequently allowing the crystalline roxithromycin to desolvate, to render the roxithromycin in an amorphous form (Form-III) of roxithromycin.

Further Details of Respective Steps in the Method According to the Invention:

The first step of the method, according to a preferred embodiment of the invention is to select roxithromycin raw material from known commercially available anhydrous or monohydrate forms.

The subsequent step of the method is to dissolve the roxithromycin in an organic solvent. It is foreseen that the organic solvent could be selected from the group consisting of 1,4-dioxane, 1-butanol, 1-propanol, 2-butanol, 2-propanol, acetic acid, acetone, acetonitrile, benzene, chloroform, dichloromethane, diethyl ether, dimethylformamide, ethanol, ethyl acetate, heptanol, hexane, hexanol, mesitylene, methanol, octanol, pentanol, petroleum ether, propionic acid, tetrahydrofuran and toluene. Applicant has found that an organic solvent in the form of chloroform is particularly suitable. Therefore, a solution of roxithromycin was prepared by dissolving roxithromycin raw material in chloroform.

In preparation of a supersaturated solution, the temperature of the solution of roxithromycin and chloroform is elevated to just below the boiling point of chloroform. The solution is stirred until the raw material of roxithromycin is dissolved.

In a subsequent step, the chloroform is allowed to slowly evaporate from the supersaturated solution resulting in a crystalline chloroform solvated form of roxithromycin. Thereafter, the solvated form of roxithromycin is allowed to desolvate resulting in an amorphous polymorphic form (Form-III) of roxithromycin.

Further Analysis and Findings

It has surprisingly been found that Form-III is significantly more soluble in water, phosphate buffer (pH 6.8) and acetate buffer (pH 4.5) compared to conventional anhydrous or monohydrate roxithromycin prepared according to prior art methods, as discussed in more detail below.

In further analysis of the novel Form-III, each of five replicate test tubes were filled with an excess of the amorphous form (Form-III) of roxithromycin and 10 ml of solubility medium. The process was performed with each of the following mediums: acetate buffer (pH 4.5), phosphate buffer (pH 6.8), distilled water and 0.1 M HCl. The phosphate buffer comprises potassium dihydrogen phosphate, disodium hydrogen phosphate and water. The acetate buffer comprises ammonium acetate, glacial acetic acid and water. This method was also used for testing the prior art anhydrous roxithromycin.

The 0.1 M HCl results for both forms were omitted due to the rapid degradation of roxithromycin therein.

The test tubes were fixed to a rotating axis (54 rpm) and submerged in a water bath at 37 degrees Celsius±2 degrees Celsius for twenty-four hours. The contents of the test tubes were filtered through a 0.45 μm filter and subsequently the respective filtrates were diluted.

The concentrations of the four filtrates of amorphous form (Form-III) of roxithromycin and roxithromycin raw material were respectively determined by HPLC (high performance liquid chromatography) assay. The HPLC assay was performed utilising a mobile phase of 30 g/L ammonium dihydrogen phosphate buffer at pH 5.3. The pH was adjusted with sodium hydroxide solution. The mobile phase comprised of buffer (600) and acetonitrile (400). A Luna C18 150 mm×4.6 mm column was used with a flow rate of 1.0 ml/min and a wavelength of 205 nm. Validation of this method provided a linear regression, $R^2$, of 0.9998.

Figure 1:
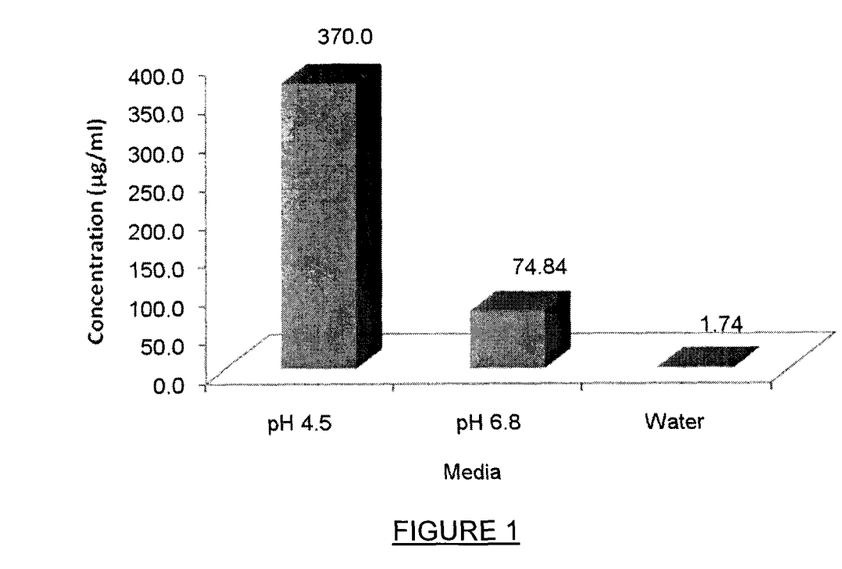
FIGS. 1 and 2: depict solubility profiles comparing the solubility of roxithromycin monohydrated raw material (FIG. 1) and the chloroform amorphous form (Form-III) of roxithromycin (FIG. 2) prepared using a method according to a preferred embodiment of the present invention (vertical axis: concentration (μg/ml); horizontal axis: media (pH))

Referring to FIG. 1, it was established that the solubility of roxithromycin monohydrate raw material is 370.0±8.3 μg/ml in acetate buffer (pH 4.5); 74.8±5.1 μg/ml in phosphate buffer (pH 6.8); and 1.7±0.6 μg/ml in distilled water.

Figure 2:
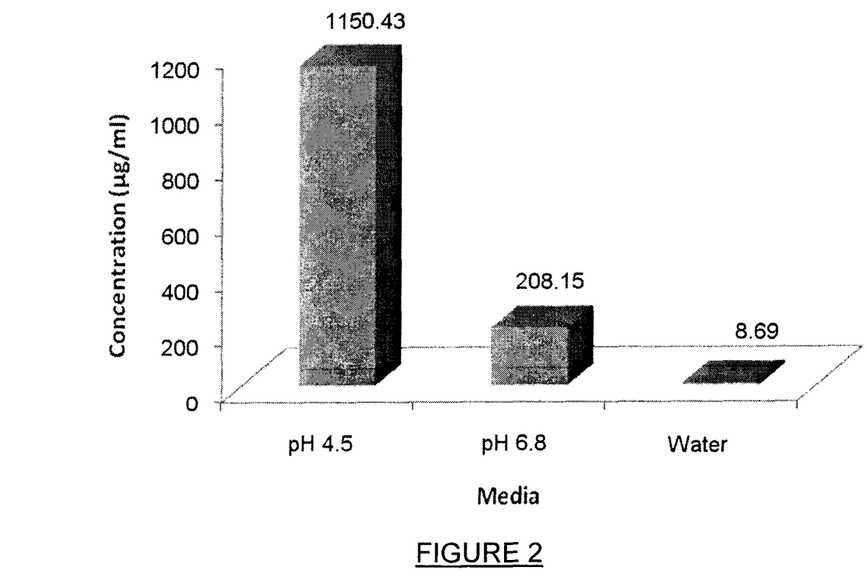

Referring to FIG. 2, the solubility of Form-III, was established as 1150.4±6.5 μg/ml in acetate buffer (pH 4.5), 208.2±3.7 μg/ml in phosphate buffer (pH 6.8) and 8.6±1.8 μg/ml in distilled water.

In comparison with the raw material of roxithromycin (FIG. 1), novel amorphous form (Form-III) of roxithromycin indicated a significant improvement in solubility with a 3.1 fold (211%) improvement in acetate buffer (pH 4.5); a 2.78 fold (178%) improvement in solubility in phosphate buffer (pH 6.8); and a 5 fold (405%) improvement in solubility in distilled water as medium. It was therefore found that the amorphous form (Form-III) of roxithromycin was at least 50%, more particularly at least 150% more soluble than anhydrous or monohydrated roxithromycin in acetate buffer and water. In fact, it was found that the amorphous form (Form-III) of roxithromycin was 211% more soluble in acetate buffer and 405% in water than anhydrous or monohydrate roxithromycin. It was further found that the amorphous form (Form-III) of roxithromycin was at least 50%, more particularly at least 100% more soluble than anhydrous roxithromycin in a phosphate buffer medium. More particularly, it was found that amorphous form (Form-III) of roxithromycin was 178% more soluble in phosphate buffer that anhydrous or monohydrate roxithromycin.

During further stability analysis, samples of both the raw material and amorphous form (Form-III) of roxithromycin were kept at 25 degrees Celsius and 75% relative humidity (RH) (FIG. 7); 30 degrees Celsius and 75% relative humidity (FIG. 8); and 40 degrees Celsius and 75% relative humidity, for a period of 4 weeks. The samples were analysed by thermogravimetric analysis (TGA) and percentage weight loss/gain was determined.

Figure 7:
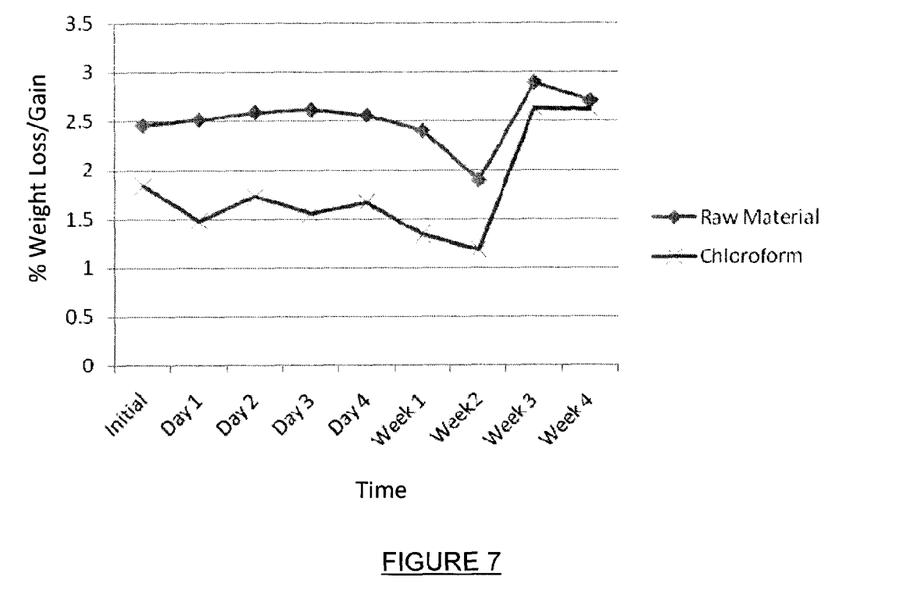
FIGS. 7 to 9: depict graphs of % weight loss/gain (vertical axis: weight loss/gain (%); horizontal axis: time); (Obtained on a Shimadzu DTG-60 (Japan) with TA60 version 2.11 software. Samples were heated from 25 degrees Celsius to 200 degrees Celsius at 10° C./min, in open aluminium crucibles. Nitrogen gas was used as inert atmosphere.)
Figure 8:
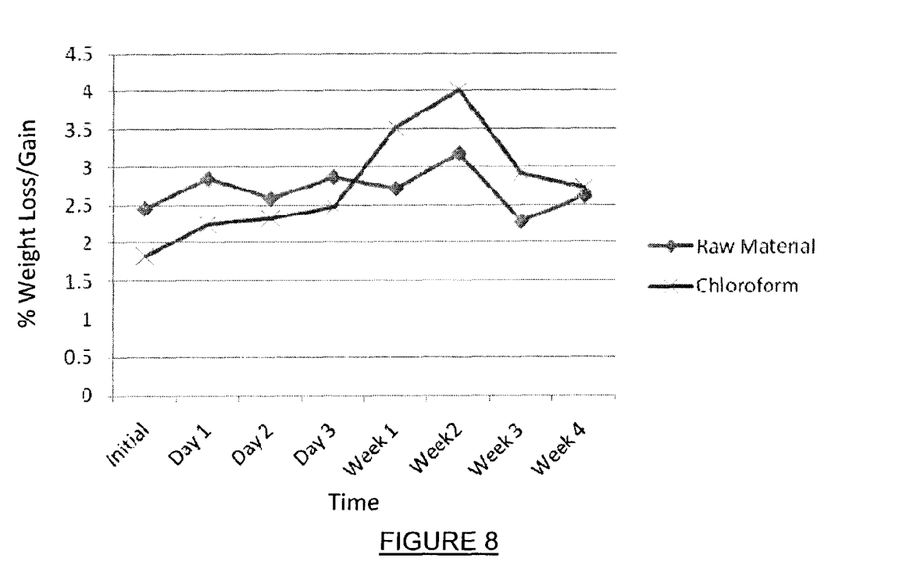
Figure 9:
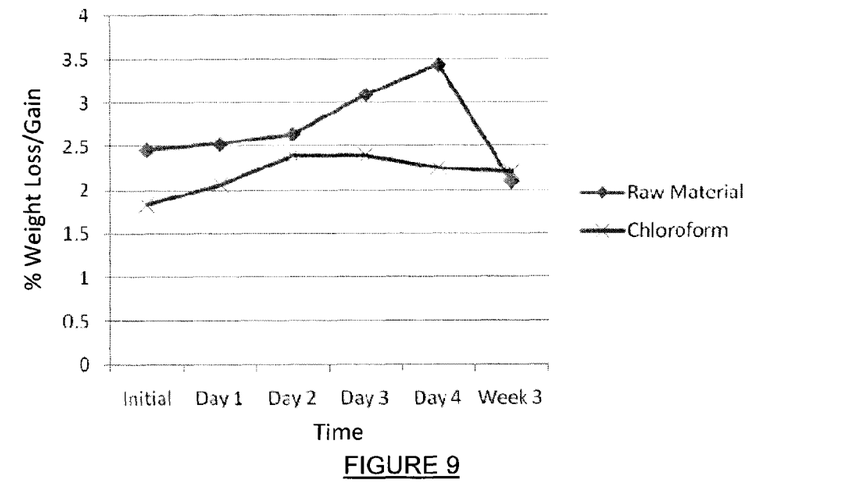

It is evident from FIGS. 7 and 8 that after week 4 of a stability trial an amount of approximately 2.5% moisture is absorbed by the samples. The TGA results obtained for the samples stored at 40° C./75% RH (FIG. 9) did however not show the same extent of moisture absorption as that obtained with the samples of FIGS. 7 and 8. The stability study indicates that the amorphous form is stable over a period of 4 weeks and did not recrystallise to a crystalline form. No moisture-induced recrystallisations of the amorphous form were observed. Furthermore, although moisture absorption did occur, the amorphous form (Form-III) did not transform to the monohydrate. The amorphous form (Form-III) could therefore be regarded as stable against increased temperatures and humidity.

Figure 3:
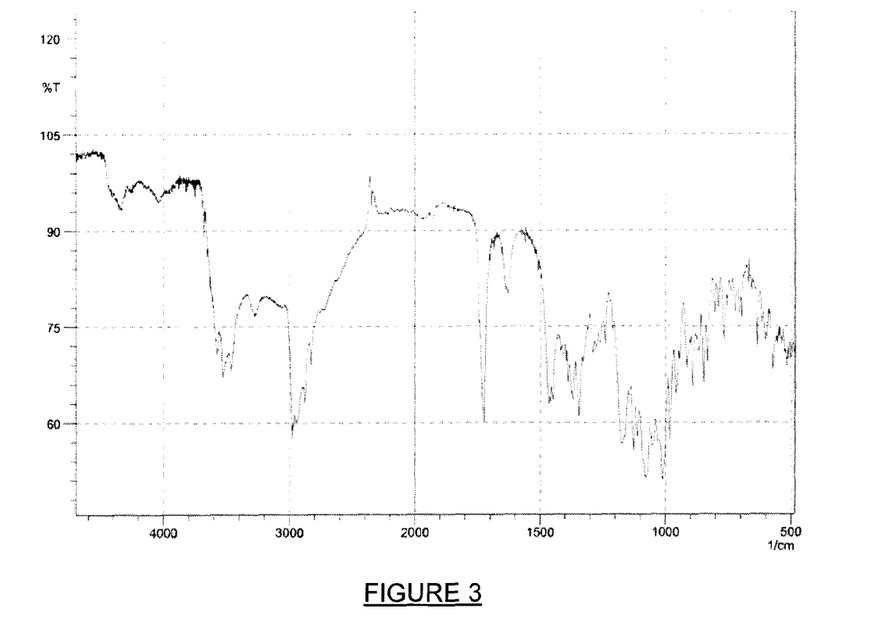
FIGS. 3 and 4: depict infra-red (IR) spectra of prior art roxithromycin monohydrate (FIG. 3) and amorphous form (Form-III) of roxithromycin (FIG. 4) (vertical axis: transmittance (percentage); horizontal axis: wavenumbers ($cm^{-1}$)); (The infra-red spectra was obtained on a Shimadzu IRPrestige-21 (Japan), using a Pike Multi-Reflectance ATR accessory, with Shimadzu IR solution version 1.40 software. Pattern was recorded over a range of 400-4000 $cm^{-1}$. KBr was used as background. The sample was dispersed in a matrix of powdered potassium bromide and, through diffuse reflectance infra-red Fourier transform spectroscopy (DRIFTS), the IR-spectrum was measured in a reflectance cell.)

From a comparison of the IR spectra of the raw material (FIG. 3) and the amorphous form (Form-III) of roxithromycin (FIG. 4) the following distinction would be drawn at the following wavenumbers:

| Anhydrous roxithromycin raw material | Amorphous form (Form-III) of roxithromycin |
| --- | --- |
| 3577.15 cm$^{-1}$ | No peak |
| 3526.03 cm$^{-1}$ | No peak |
| 3465.27 cm$^{-1}$ | No peak |
| 3276.24 cm$^{-1}$ | No peak |

The IR data illustrates that the absorbed moisture was not structurally absorbed within the molecule, but only absorbed on the surface of the structure. This is confirmed by the peak between wavenumbers 3580 to 3464 cm$^{-1}$ that represents the —OH bands of roxithromycin raw material and the lack of peaks in the amorphous form (Form-III) of roxithromycin. This indicates that the additional moisture/mass detected in the samples is not structurally bound. This confirms the fact that the moisture absorbed during the stability trial did not induce recrystallisation of the amorphous form and also did not induce the transformation of the amorphous form to the monohydrate of roxithromycin.

Figure 5:
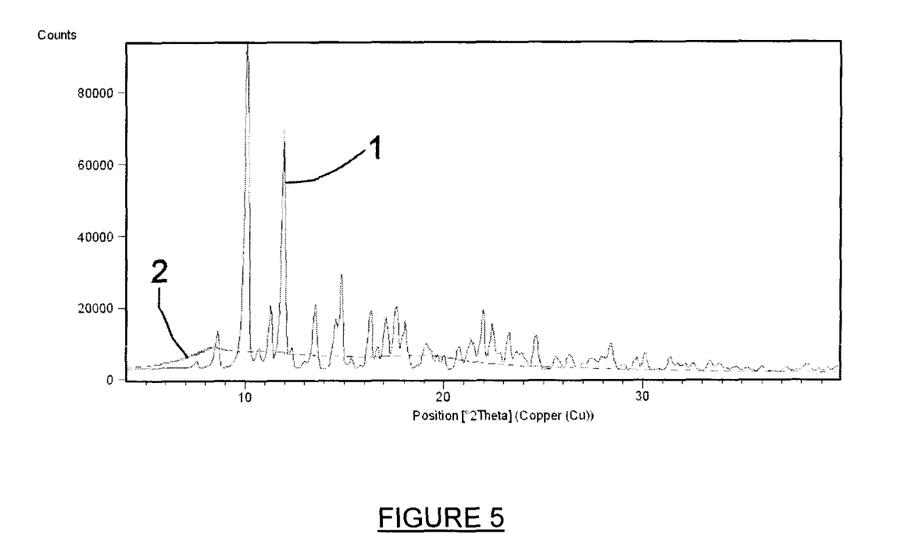
FIG. 5: depicts an XRPD (x-ray powder diffraction pattern) overlay pattern of prior art roxithromycin (1) and amorphous form (Form-III) of roxithromycin (2) prepared according to a preferred embodiment of the invention (vertical axis: intensity (CPS); horizontal axis: 2 Theta (degrees)) (Obtained on a PANalytical Xpert-Pro, Goniometer=PW3050/60 (Theta/Theta); Minimum step size 2 Theta:0.001; Measurement Temperature [° C.]:25.00, Anode Material: Cu, K-Alpha1 [Å]:1.54060, K-Alpha2 [Å]: 1.54443, K-Beta [Å]: 1.39225, K-A2/K-A1 Ratio: 0.50000, Generator Settings: 45 mA, 40 kV, Diffractometer Type: 0000000011018023, Goniometer Radius [mm]:240.00, Dist. Focus-Diverg. Slit [mm]: 91.00, Incident Beam Monochromator: No, Spinning: Yes)

FIG. 5 depicts the XRPD data obtained for both roxithromycin raw material and the amorphous form (Form-III) of roxithromycin. It is evident from the figure that no recrystallisation of the amorphous form (Form-III) of roxithromycin occurred over a storage time of four weeks at 40 degrees Celsius and 75% relative humidity. The stability test therefore indicates that the amorphous form (Form-III) of roxithromycin remained structurally stable as an amorphous form.

Figure 6:
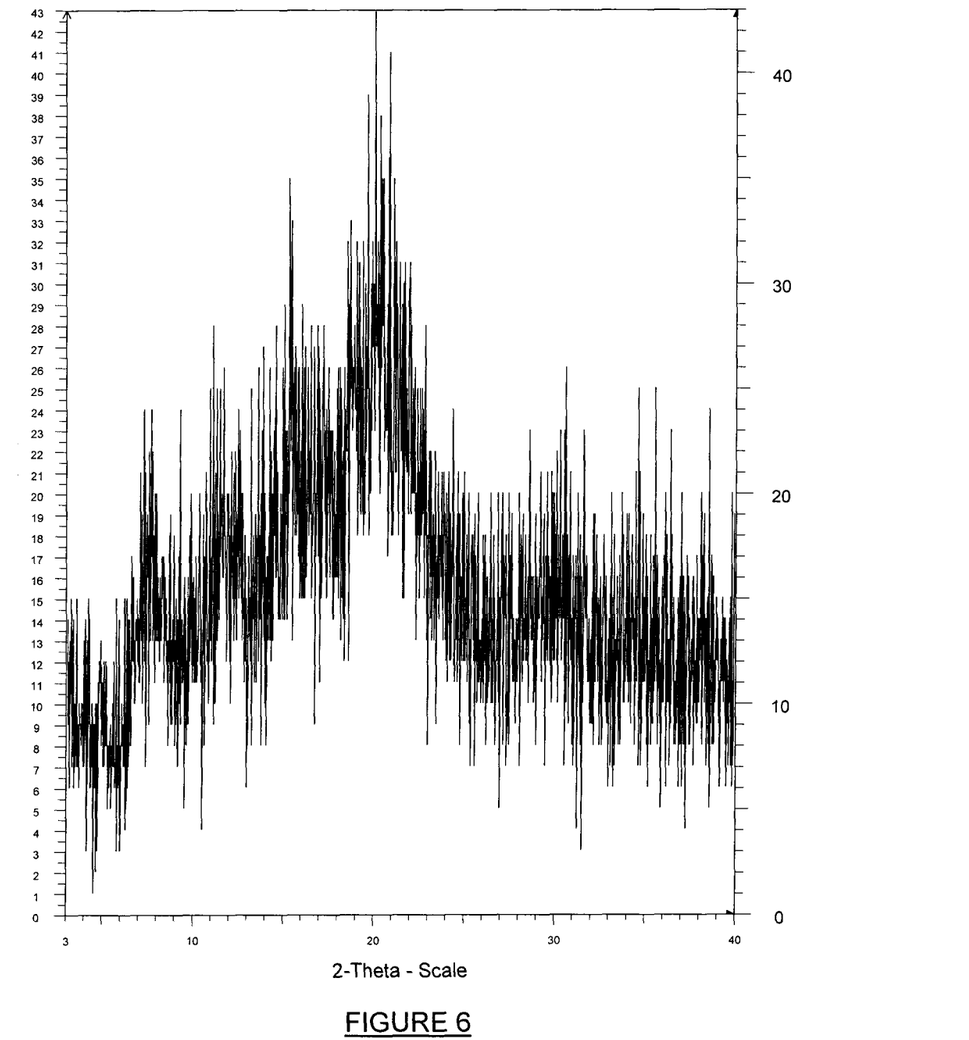
FIG. 6: depicts a characteristic XRPD of amorphous form (Form-III) of roxithromycin (vertical axis: intensity (Lin (counts)); horizontal axis: 2 Theta (degrees))
Figure 10:
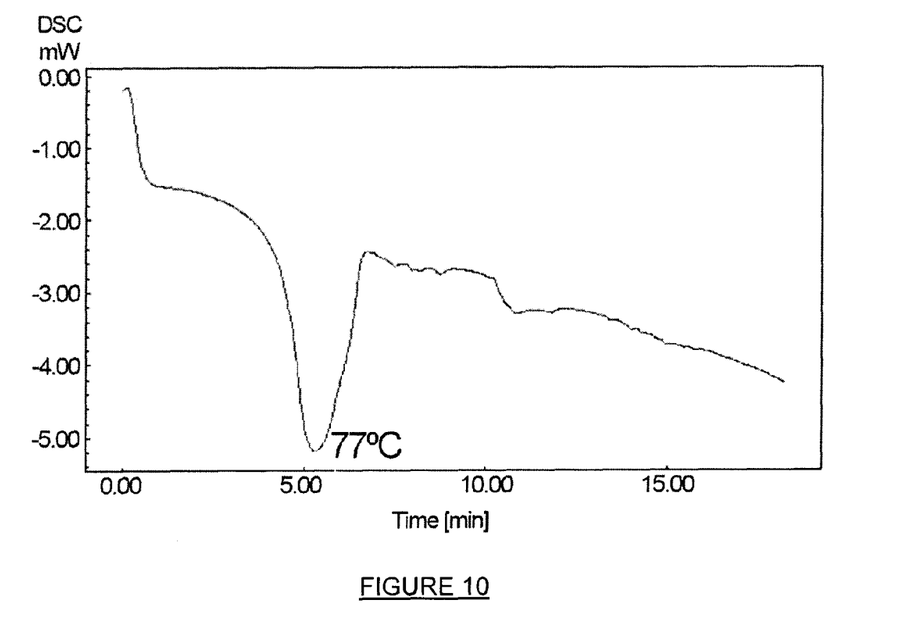
FIG. 10: depicts a DSC (differential scanning calorimetry) thermogram obtained for the said Form-III (vertical axis: heat flow (W/g); horizontal axis: time (min)) (DSC trace obtained on a Shimadzu DSC-60A (Japan) with TA60 version 2.11 software. Approximately 2 to 4 mg of each sample was weighed and heated in open aluminium crucibles. Samples were heated at 2° C./min in an inert nitrogen atmosphere.)

Referring to FIG. 6, it is evident from the low intensity levels and characteristic halo of the XRPD pattern that Form-III of roxithromycin is an amorphous structure. The amorphous structure of Form-III is further confirmed with the DSC trace's (FIG. 10). The melting point obtained for this form is lower than that of the raw material (approximately 119° C.).

Figure 12:
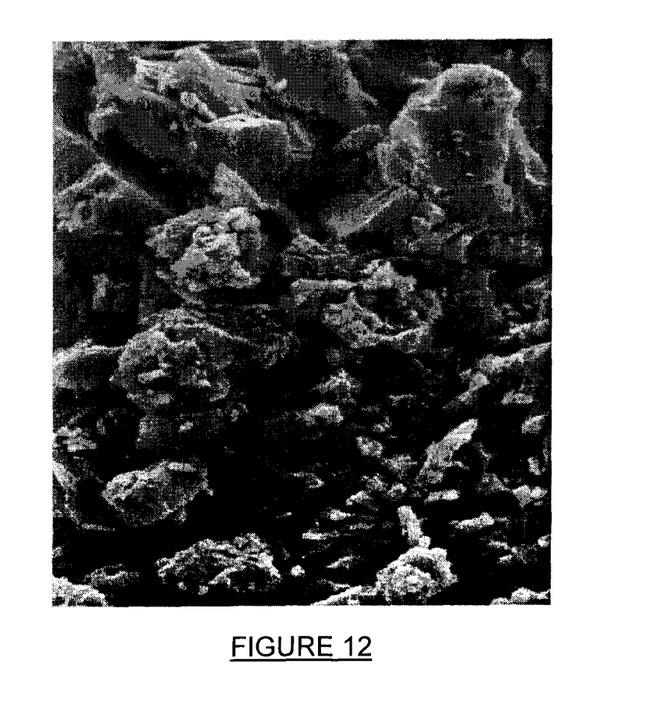
Figure 13:
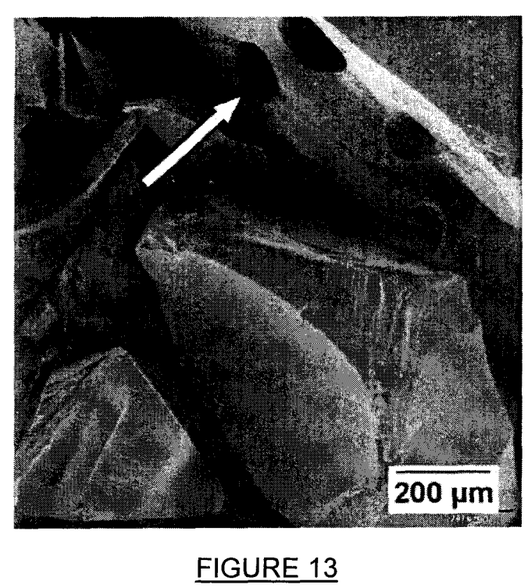

Scanning electron microscope (SEM) images compared roxithromycin raw material (monohydrate) according to the prior art (FIG. 11) to solvated amorphous roxithromycin (FIG. 12) and to desolvated amorphous form (Form-III) (FIG. 13).

Figure 11:
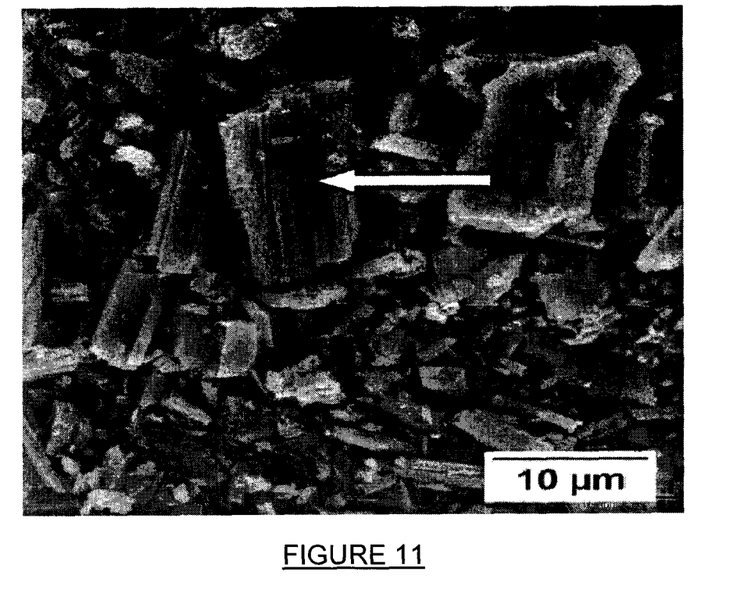
FIGS. 11 to 13: depict SEM (scanning electron microscope) images comparing roxithromycin raw material (monohydrate) according to the prior art (FIG. 11) to solvated amorphous roxithromycin (FIG. 12) and to desolvated amorphous form (Form-III) (FIG. 13).

The arrow in FIG. 11 illustrates the presence of the solvent channels in the raw material (monohydrate). This is also known as a striated appearance. The channels tend to attract water molecules creating a monohydrate structure, which is generally regarded as being poorly water soluble.

Desolvated amorphous form (Form-III) of roxithromycin (FIG. 13) has a smooth glass-like appearance. The lack of solvent channels limits the attraction of water molecules. This is indicative of the fact that, although moisture was absorbed by the sample during a 4 week stability trial, this absorbed moisture did not bind to the roxithromycin molecule, due to the absence of the solvent channels. Form-III is therefore also more water soluble than the prior art raw material of roxithromycin.

Amorphous form (Form-III) of roxithromycin is formulated for administration in any convenient way and the invention includes, within its scope, pharmaceutical compositions comprising amorphous form (Form-III) of roxithromycin for use in human or veterinary medicine.

The pharmaceutical compositions are presented for use in a conventional manner with the aid of a pharmaceutically acceptable carrier or excipient and may also contain, if required, other active ingredients. The amorphous form (Form-III) of roxithromycin is typically formulated for oral, buccal, topical or parenteral administration.

Oral administration is the preferred dosage form, particularly in the form of tablets and capsules. The pharmaceutical composition for oral administration conveniently takes the form of tablets, capsules, powders, solutions, syrups or suspensions prepared by conventional means with acceptable excipients. Buccal administration compositions take the form of tablets or lozenges formulated in conventional manner.

The amorphous form (Form-III) of roxithromycin is further formulated for parenteral administration by bolus injection or continuous infusion. Formulations for injection are presented in unit dosage forms in ampoules, or in multi-dose containers, with an added preservative. The compositions further take such forms as suspensions, solutions or emulsions in oily or aqueous vehicles, and contain formulatory agents such as suspending, stabilising and/or dispersing agents. Alternatively, the active ingredient is in powder form for reconstitution with a suitable vehicle.

The amorphous form (Form-III) of roxithromycin is yet further formulated in topical applications, comprising ointments, creams, gels, lotions, powders, transdermal patches, dermal patches or sprays prepared in a conventional manner.

The amorphous form (Form-III) of roxithromycin is yet further formulated in rectal and vaginal compositions such as suppositories or retention enemas containing conventional suppository bases such as cocoa butter or other glycerides.

For oral administration a convenient daily dosage regime of amorphous form (Form-III) of roxithromycin is a total of 150 mg 2 times per day for 5 days, dependent upon the age and condition of a patient.

The amorphous form (Form-III) of roxithromycin prepared in accordance with the method of the present invention is formulated into a medicament and used in a method of treating a patient suffering from a bacterial infection by administering to the patient a pharmaceutically effective amount thereof of a total of 150 mg 2 times per day for 5 days, dependent upon the age and condition of the patient.

It will be appreciated that the disadvantages associated with prior art forms of roxithromycin, namely anhydrous and monohydrate forms, could be alleviated with the method according to the invention. In particular, the absorption and bioavailability of roxithromycin could be increased due to increased water, acetate buffer and phosphate buffer solubility of the new amorphous polymorphic form (Form-III) of roxithromycin described in this application.

Moreover, reduced quantities of the amorphous form (Form-III) of roxithromycin are needed, resulting not only in reduced risk of side-effects, but also reduced cost of treatment.

It is further foreseen that amorphous form (Form-III) of roxithromycin would not only present a relatively cheaper alternative to conventional production and manufacturing methods, but would also present a product that is superior in solubility to conventional anhydrous and monohydrate forms of roxithromycin.

Applicant thus foresees that a method according to the invention for preparing amorphous form (Form-III) of roxithromycin would not only present a relatively cheaper alternative to conventional production and manufacturing methods, but would also present a product that is superior in respect of solubility to conventional anhydrous or monohydrate forms of roxithromycin.

It will be appreciated further that variations in detail are possible with a method for preparing a medicament and a medicament prepared with such a method, according to the invention without departing from the scope of the appended claims.

The invention claimed is:

1. A method of preparing amorphous roxithromycin including the steps of providing roxithromycin selected from the group consisting of anhydrous roxithromycin or monohydrated roxithromycin; preparing a supersaturated solution of the roxithromycin in an organic solvent in the form of chloroform; allowing the chloroform to evaporate to render the roxithromycin in a crystalline, chloroform-solvated form; and allowing the crystalline roxithromycin to desolvate, to render the roxithromycin in an amorphous form characterized by the absence of recrystallization after preparation, for a period of 4 weeks at 40 degrees Celsius and 75% relative humidity.

2. The method of preparing amorphous roxithromycin of claim 1 wherein the step of preparing the supersaturated solution of the roxithromycin in chloroform includes the step of elevating the temperature of the solution to just below the boiling point of chloroform.

3. Amorphous roxithromycin prepared by the method of claim 1 further characterized by having increased solubility relative to said anhydrous roxithromycin or monohydrated roxithromycin and which displays an infra-red pattern substantially as depicted in FIG. 4.

4. Amorphous roxithromycin of claim 3 characterized by the absence of peaks in the infra-red spectrum of roxithromycin at 3577; 3526; 3465 and 3276.24 cm$^{-1}$ relative to the infra-red spectrum of the prior art roxithromycin raw material displaying peaks at 3577; 3526; 3465 and 3276.24 cm$^{-1}$.

5. Amorphous roxithromycin of claim 3 having at least 50% increased solubility over anhydrous and monohydrated roxithromycin in acetate buffer (pH 4.5).

6. Amorphous roxithromycin of claim 5 having at least 150% increased solubility over anhydrous and monohydrated roxithromycin in acetate buffer (pH 4.5).

7. Amorphous roxithromycin of claim 3 having at least 50% increased solubility over anhydrous and monohydrated roxithromycin in phosphate buffer (pH 6.8).

8. Amorphous roxithromycin of claim 7 having at least 100% increased solubility over anhydrous and monohydrated roxithromycin in phosphate buffer (pH 6.8).

9. Amorphous roxithromycin of claim 3 having at least 50% increased solubility over anhydrous and monohydrated roxithromycin in water.

10. Amorphous roxithromycin of claim 9 having at least 150% increased solubility over anhydrous and monohydrated roxithromycin in water.

11. A composition prepared from the stable amorphous roxithromycin of claim 3 together with at least one inert pharmaceutically acceptable carrier or diluents in a dosage form selected from the group consisting of tablets; capsules; powders; solutions; syrups; suspensions; bolus injections; continuous infusions; powder for reconstitution; ointments; creams; gels; lotions; sprays; enemas, douche, pessaries, transdermal patches, dermal patches and lozenges.

12. A method of treating a patient suffering from a bacterial infection comprising administering to said patient a pharmaceutically effective amount of amorphous roxithromycin according to claim 3.

* * * * *